United States Patent [19]

Koppel

[11] 4,029,651

[45] June 14, 1977

[54] PROCESS FOR PREPARING 3-ACYLOXYMETHYL-2-CEPHEM COMPOUNDS

[75] Inventor: Gary A. Koppel, Indianapolis, Ind.

[73] Assignee: Eli Lilly and Company, Indianapolis, Ind.

[22] Filed: Jan. 19, 1976

[21] Appl. No.: 650,583

[52] U.S. Cl. .................. 260/243 C; 260/239.1
[51] Int. Cl.² ........................ C07D 501/04
[58] Field of Search .................. 260/243 C

[56] References Cited

UNITED STATES PATENTS

| | | | |
|---|---|---|---|
| 3,883,518 | 5/1975 | Ponticello | 260/243 C |
| 3,933,806 | 1/1976 | Spry | 260/243 C |

*Primary Examiner*—Nicholas S. Rizzo

*Attorney, Agent, or Firm*—William C. Martens, Jr.; Everet F. Smith

[57] ABSTRACT

A 3-exomethylenecepham sulfoxide ester is reacted with a mixture of a carboxylic acid of the formula

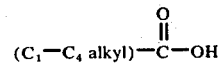

and the corresponding anhydride of said carboxylic acid at a temperature of from about 70° C. to about 130° C. to produce the corresponding 3-acyloxymethyl-Δ²-cephem. This product is useful as an intermediate in the preparation of antibiotically active cephalosporins.

13 Claims, No Drawings

PROCESS FOR PREPARING 3-ACYLOXYMETHYL-2-CEPHEM COMPOUNDS

BACKGROUND OF THE INVENTION

Cephalosporin antibiotics having an acyloxymethyl group at the $C_3$ carbon atom of the cephem nucleus are well recognized in the cephalosporin art, see, for example, U.S. Pat. Nos. 3,270,009; 3,278,531; 3,532,694; 3,705,897; 3,728,342; and 3,795,672. New methods for preparing these cephalosporins continually are being sought. This invention is directed to a process for preparing 3-acyloxymethyl-$\Delta^2$-cephem compounds, which compounds are readily convertible by recognized techniques to the aforementioned 3-acyloxymethyl cephalosporin antibiotics.

Recently, 3-exomethylenecepham esters have been described, for example, in Chauvette et al., J. Org. Chem. 38 2994 (1973); and in U.S. Pat. No. 3,792,995. These compounds have the general formula

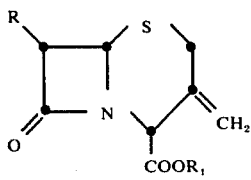

The corresponding sulfoxides are starting materials employed in the process of this invention and are readily available from the corresponding 3-exomethylenecepham esters by known methods. For example, a 3-exomethylenecepham acid or ester can be reacted with a peracid, for example, m-choroperbenzoic acid, perbenzoic acid, peracetic acid, and the like, to form the corresponding sulfoxide. The 3-exo double bond of the starting material is inert under these conditions of sulfoxide formation, and, consequently, the sulfoxide is prepared by the selective oxidation of the sulfide.

The sulfoxide ester starting materials alternatively and preferably are prepared by a process described by S. Kukolja in co-pending Applications Ser. Nos. 536,273 and 536,280, both filed Dec. 24, 1974 and both now abandoned. According to these described methods, a penicillanic acid ester sulfoxide is reacted with an N-chloro halogenating agent in a dry, inert organic solvent at a temperature between about 70° C. and about 100° C. to provide an azetioinone sulfinyl chloride. The sulfinyl chloride then is reacted with a Lewis acid Friedel-Crafts type catalyst in a dry, inert, organic solvent to effect cyclization and to provide the 3-exomethylenecepham sulfoxide ester.

As indicated, the 3-exomethylenecepham sulfoxide esters represent the starting materials of the process of this invention, and it has now been discovered that it is possible to convert these sulfoxide esters to their corresponding 3-acyloxymethyl-$\Delta^2$-cephems, which class of compounds is useful as intermediates in the preparation of the aforementioned 3-acyloxymethyl cephalosporins (3-acyloxymethyl-$\Delta^3$-cephem compounds).

SUMMARY OF THE INVENTION

Therefore, this invention relates to a process for preparing $\Delta^2$-cephem compounds. In particular, it relates to a process for the preparation of 3-acyloxymethyl-$\Delta^2$-cephem esters, useful as intermediates for the preparation of cephalosporin antibiotics.

Accordingly, therefore, this invention is directed to a process for preparing a compound of the formula

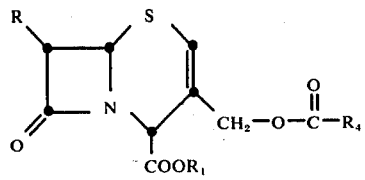

which comprises reacting a 3-exomethylenecepham sulfoxide of the formula

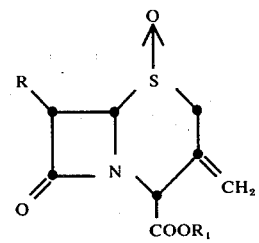

with a mixture of a carboxylic acid of the formula

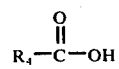

and the corresponding anhydride of said carboxylic acid at a temperature of from about 70° C. to about 130° C., in which, in the above formulae, $R_4$ is $C_1$–$C_4$ alkyl, $R_1$ is a carboxylic acid protecting group, and R is b 1. an imido group of the formula

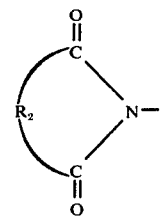

in which $R_2$ is $C_2$–$C_4$ alkenylene or 1,2-phenylene;

2. an amido group of the formula

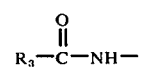

in which $R_3$ is a. hydrogen, $C_1$–$C_3$ alkyl, halomethyl, benzyloxy, 4-nitrobenzyloxy, 2,2,2-trichloroethoxy, 4-methoxybenzyloxy, 3-(2-chlorophenyl)-5-methylisoxazol-4-yl;

b. the group R' in which R' is phenyl or phenyl substituted with 1 or 2 halogens, nitro, cyano, trifluoromethyl, $C_1$–$C_4$ alkyl, or $C_1$–$C_4$ alkoxy;

c. a group of the formula R'—(O)$_m$—CH$_2$— in which R' is defined above and m is 0 or 1;

d. a group of the formula

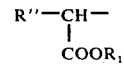

in which R'' is R' as defined above, 2-thienyl, or 3-thienyl, and $R_1$ is as defined above; or e. a group of the formula R'''-CH₂- in which R''' is 2-thienyl, 3-thienyl, 2-furyl, 3-furyl, 2-thiazolyl, 5-tetrazolyl, 1-tetrazolyl, or 4-isoxazolyl; or R is 3. an imidazolidinyl group of the formula

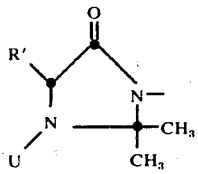

in which R' is as defined above and U is nitroso or acetyl.

DETAILED DESCRIPTION OF THE INVENTION

As indicated above, in the process of this invention, a 3-exomethylenecepham ester sulfoxide represented by the following general formula

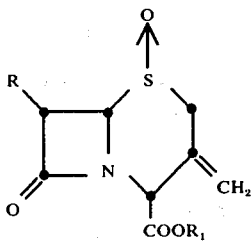

is converted to a 3-acryloxymethyl-Δ²-cephem ester represented by the following structural formula

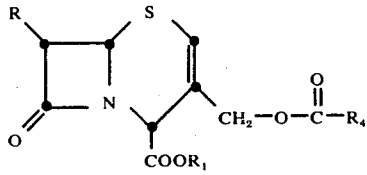

R₁ in the above formulae denotes a carboxylic acid protecting group, and, preferably, one which is removable by hydrogenation. Preferred carboxylic acid protecting groups include, for example, 2,2,2-trihaloethyl, benzyl, p-nitrobenzyl, succinimidomethyl, phthalimidomethyl, p-methoxybenzyl, C₂–C₆ alkanoyloxymethyl, dimethylallyl, phenacyl, or p-halophenacyl, in any of the above of which halo denotes chlorine, bromine or iodine.

Specific illustrations of the preferred carboxylic acid protecting groups include, for example, 2,2,2-trichloroethyl, 2,2,2-tribromoethyl, benzyl, p-nitrobenzyl, succinimidomethyl, phthalimidomethyl, p-methoxybenzyl, acetoxymethyl, pivaloyloxymethyl, propionoxymethyl, phenacyl, p-chlorophenacyl, p-bromophenacyl, and the like.

Highly preferred carboxylic acid protecting groups are benzyl, p-nitrobenzyl, p-methoxybenzyl, 2,2,2-trichloroethyl, phenacyl, p-chlorophenacyl, and p-bromophenacyl.

Most preferred carboxylic acid protecting groups are p-nitrobenzyl and 2,2,2-trichloroethyl.

The group R in the 7-position of the 3-exomethylenecepham sulfoxide starting materials and the 3-acyloxy methyl-Δ² -cephem products is, in part, defined as

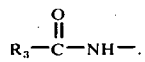

Specific illustrations of the group R₃ include, for example, hydrogen, methyl, ethyl, n-propyl, isopropyl, chloromethyl, bromomethyl, benzyloxy, 4-nitrobenzyloxy, 2,2,2-trichloroethoxy, 4-methoxybenzyloxy, phenyl, 2-chlorophenyl, 3,4-dichlorophenyl, 3-chloro-4-fluorophenyl, 4-nitrophenyl, 2-cyanophenyl, 4-trifluoromethylphenyl, 3-methylphenyl, 2-ethylphenyl, 4-n-propylphenyl, 4-t-butylphenyl, 2-methoxyphenyl, 4-ethoxyphenyl, 3-isopropyloxyphenyl, 4-isobutyloxyphenyl, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-isopropoxybenzyl, phenoxymethyl, 3-iodophenoxymethyl, 4-fluorophenoxymethyl, 3-chloro-4-fluorophenoxymethyl, 2,5-dichlorophenoxymethyl, 3-isopropoxyphenoxymethyl, 4-ethylphenoxymethyl, 4-chlorophenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, α-(benzyloxycarbonyl)-thien-2-ylmethyl, α-(4-nitrobenzyloxycarbonyl)-thien-2-ylmethyl, α-(4-methoxybenzyloxycarbonyl)-thien-2-ylmethyl, α-(phenacyloxycarbonyl)-thien-3-ylmethyl, α-(4-nitrobenzyloxycarbonyl)-thien-3-ylmethyl, α-(benzyloxycarbonyl)-thien-3-ylmethyl, α-(acetoxymethoxycarbonyl)-thien-2-ylmethyl, α-(benzyloxycarbonyl)-benzyl, α-(4-nitrobenzyloxycarbonyl)benzyl, α-(4-methoxybenzyloxycarbonyl)benzyl, α-(2,2,2-trichloroethoxycarbonyl)benzyl, α-(p-chlorophenacyloxycarbonyl)-4-bromobenzyl, α-(benzyloxycarbonyl)-3-chlorobenzyl, α-(4-nitrobenzyloxycarbonyl)-4-fluorobenzyl, α-(4-nitrobenzyloxycarbonyl)-3-methoxybenzyl, α-(4-methoxybenzyloxycarbonyl)-4-isopropoxybenzyl, α-benzyloxycarbonyl-3-nitrobenzyl, α-(4-nitrobenzyloxycarbonyl)-2-cyanobenzyl, α-(p-bromophenacyloxycarbonyl)-4-trifluoromethylbenzyl, α-(4-nitrobenzyloxycarbonyl)-4-methylbenzyl, α-benzyloxycarbonyl-3-n-butylbenzyl, α-(benzyloxycarbonyl)-4-methoxybenzyl, α-(4-nitrobenzyloxycarbonyl)-3-isopropoxybenzyl, thien-2-ylmethyl, thien-3-ylmethyl, fur-2-ylmethyl, fur-3-ylmethyl, thiazol-2-ylmethyl, tetrazol-5-ylmethyl, tetrazol-1-ylmethyl, isoxazol-4-ylmethyl, 3-(2-chlorophenyl)-5-methylisoxazol-4-yl, and the like.

In portions of the definition of this invention, the group —COOR₁ appears. This represents a "protected carboxy" group.

The term "protected carboxy," refers to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrogenolytic methods. Examples of carboxylic acid protecting groups include benzyl, 4-methoxybenzyl, C₂–C₆ alkanoyloxymethyl, 4-nitrobenzyl, phenacyl, p-halophenacyl, dimethylallyl, 2,2,2-trichloroethyl, succinimidomethyl, and like ester forming moieties. The nature of such ester forming groups is not critical so long as the ester formed therewith is stable under the reaction conditions of the process of this invention. Furthermore, other known carboxy protecting groups such as those described by E. Haslam in *Protective Groups in Organic Chemistry*, supra, Chapter 5, are considered to be within the term "protected carboxy" as used herein.

Preferred $R_1$ groups which participate in the overall definition of the term "protected carboxy" are 4-methoxybenzyl, 4-nitrobenzyl, 2,2,2-trichloroethyl, phenacyl, and p-halophenacyl.

In the foregoing discussion, carboxy protecting groups, of course, are not exhaustively described. The function of these groups is to protect reactive functional groups during preparation of a desired product. They then can be removed without disruption of the remainder of the molecule. Many such protecting groups are well known in the art, and their use is equally applicable in the process of this invention.

The process of this invention also can be carried out using 3-exomethylenecepham sulfoxides having the above formula in which R is a cyclic imido group of the formula

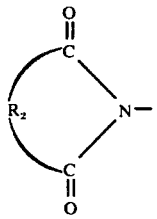

This cyclic amido group, defined by $R_2$ taken together with the nitrogen-carbonyl combination to which it is bonded, can be formed by reacting the 6-amino group of a 6-amino-3-exomethylenecepham ester with a dicarboxylic acid or anhydride or other reactive variant thereof, followed by reacting the resulting derivative with a $C_1$ to $C_4$ alkyl haloformate, for example, ethyl chloroformate, in the presence of an organic base. $R_2$ is $C_2$–$C_4$ alkenylene or 1,2-phenylene and can be considered as being the residue of a dicarboxylic acid, the cyclic imide thus represented being prepared from such dicarboxylic acid, its anhydride, or an appropriate reactive variant thereof. Cyclic imides can be prepared, for example, from acids such as maleic, methylmaleic, phthalic, and the like, or their respective anhydrides, as well as related compounds and compounds of similar reactivities. Additional examples of cyclic anhydrides of the type defined are found in the prior art, such as in the *Journal of Organic Chemistry*, Volume 26, pp. 3365–3367 (September, 1961).

In addition, the group R in the process of this invention can be an imidazolidinyl group of the formula

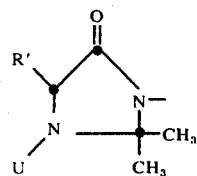

in which U is nitroso or acetyl and R' is phenyl or phenyl substituted with 1 or 2 halogens, nitro, cyano, trifluoromethyl, $C_1$–$C_4$ alkyl, or $C_1$–$C_4$ alkoxy.

The group thus represented is a 2,2-dimethyl-3-nitroso-5-oxo-4-(substituted)-imidazolidin-1-yl group or a 2,2-dimethyl-3-acetyl-5-oxo-4-(substituted)-imidazolidin-1-yl group, and the 4-substituent (R') in the imidazolidinyl formula typically includes phenyl, 3-bromophenyl, 2-chlorophenyl, 4-fluorophenyl, 3-iodophenyl, 3-chloro-4-fluorophenyl, 2-chloro-4-bromophenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-n-propoxyphenyl, 3-iospropoxyphenyl, 4-isobutoxyphenyl, and the like.

The 3-exomethylenecepham sulfoxide starting materials of the process of this invention in which R is the aforedescribed imidazolidinyl group can be prepared in accordance with known techniques by reacting an exomethylenecepham of the formula

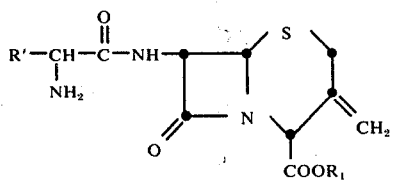

or its corresponding free acid with acetone under moderately basic conditions to produce the labile intermediate of the formula

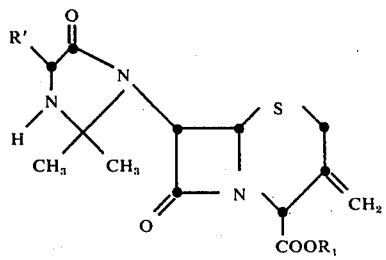

This product then is converted to the stable N-nitroso or N-acetyl derivative in which R is the aforedescribed imidazolidinyl group by treating the product wth sodium nitrite or acetic anhydride under acidic conditions and with cooling. The resulting product then can be oxidized to the corresponding sulfoxide by well recognized techniques. These preparations are detailed in Gottstein et al., J. Org. Chem., 37 (1972) 2765; and Heusler, *Helvetica Chimica Acta*, 55 (1972) 388.

As will be apparent to those of ordinary skill in the penicillin and cephalosporin arts, any of the 3-exomethylenecepham sulfoxide starting materials used in the process of this invention are readily preparable from available penicillin sources, such as naturally occurring Penicillin G and/or Penicillin V.

6-Aminopenicillanic acid (6-APA) can be prepared from either of the above naturally-occurring penicillins by cleavage of the 6-acyl function employing techniques well known in the art.

It is possible to prepare, by widely recognized techniques and from 6-APA, any of the starting materials of the process of this invention. For example, 6-APA can be converted to the desired ester by esterification of the 3-carboxyl function employing any of several typical esterification techniques.

Furthermore, the amino group of 6-APA can be acylated to produce any of the groups defined herein by the term R. This is achieved by reacting 6-APA with an activated form of the acid of the intended acyl group. Such activated forms include the corresponding acid halides, anhydrides, or activated esters, such as the pentachlorophenyl ester.

Likewise, the penicillin can be oxidized to the sulfoxide under any of a wide variety of recognized conditions, including treatment of the penicillin with m-chloroperbenzoic acid or sodium periodate.

These conversions, cleavage of 6-APA, esterification, acylation, and oxidation, can be carried out in any sequence consistent with the intended structural modifications. In any event, all such conversions can be accomplished employing techniques, conditions, and reagents readily available to and well recognized by one of ordinary skill in the art.

Once the penicillin sulfoxide ester of the formula

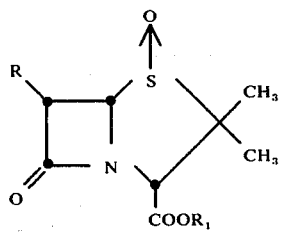

has been obtained, it can be converted to the corresponding 3-exomethylenecepham sulfoxide by treatment in accordance with the aforementioned method of S. Kukolja as delineated in co-pending Applications Ser. Nos. 536,273 and 536,280, both filed Dec. 24, 1974 and both now abandoned. According to the described method, a 6-amido- or 6-imido-penicillin ester sulfoxide is reacted with an N-chloro halogenating agent such as N-chlorosuccinimide or N-chlorophthalimide in a dry, inert solvent, such as 1,1,2-trichloroethane or toluene, at a temperature of from about 75° C. to about 135° C. to provide an azetidinone sulfinyl chloride of the formula

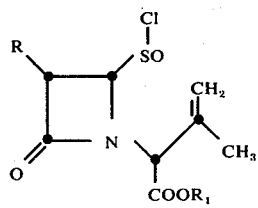

The sulfinyl chloride then is reacted with a Lewis acid Friedel-Crafts type catalyst in a dry, inert, organic solvent to effect cyclization and to provide the desired 3-exomethylenecepham sulfoxide ester, a starting material of the process of this invention.

Lewis acid Friedel-Crafts catalysts which are useful in the cyclization of the azetidinone sulfinyl chloride include, for example, stannic chloride, zinc chloride, zinc bromide, titanium tetrachloride, and zirconium chloride. Stannic chloride is the preferred catalyst for cyclization. The cyclization is carried out at a temperature of from about 20° C. to about 85° C. and in an inert solvent, preferably an aprotic organic solvent, for example, an aromatic hydrocarbon such as benzene, toluene, xylene, and the like; or a halogenated aliphatic hydrocarbon such as methylene chloride, 1,2-dichloroethane, 1,1,2-trichloroethane, and the like.

As an example of the foregoing preparation of a starting material useful in this process, a solution of p-nitrobenzyl 6-phenoxyacetamidopenicillanate sulfoxide in dry toluene is treated with 1.1 molar equivalents of N-chlorosuccinimide, and the reaction mixture is refluxed for about 90 minutes. The reaction mixture containing p-nitrobenzyl 3-methyl-2-(2-chlorosulfinyl-4-oxo-3-phenoxyacetamido-1-azetidinyl)-3-butenoate (the sulfinyl chloride intermediate), is cooled to a temperature of about 50° C., and 1.1 molar equivalents of anhydrous stannic chloride are added. The mixture thus obtained is stirred at room temperature for about 90 minutes. Water and ethyl acetate are added to the reaction mixture, and the organic layer is separated. The organic layer containing the product is washed with dilute acid, dilute sodium bicarbonate solution, and then with brine. The washed organic layer then is dried and evaporated to yield p-nitrobenzyl 7-phenoxyacetamido-3-exomethylenecepham-4-carboxylate-1-oxide.

Preferred 3-exomethylenecepham sulfoxide esters for use as starting materials in the process of this invention are those having the formula

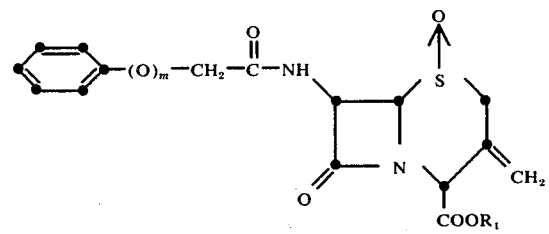

in which $m$ is 0 or 1 and $R_1$ is a carboxylic acid protecting group.

Correspondingly, the preferred 3-acyloxymethyl-$\Delta^2$-cephem ester products obtained from the process of this invention are those of the formula

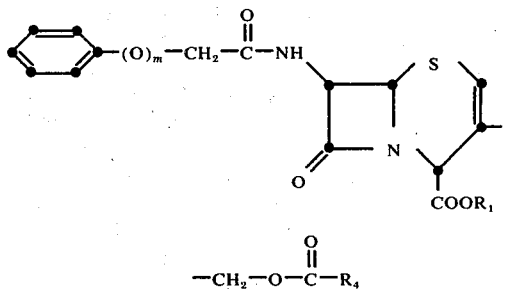

in which $m$ is 0 or 1, $R_1$ is a carboxylic acid protecting group, and $R_4$ is $C_1$–$C_4$ alkyl, and, more preferably, methyl.

Another class of preferred 3-exomethylenecepham sulfoxide esters for use in the process of this invention are those having the formula

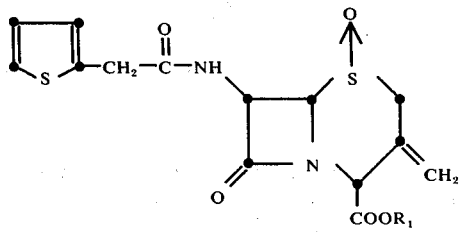

in which $R_1$ is a carboxylic acid protecting group.

The 3-acyloxymethyl-$\Delta^2$-cephem esters produced from the aforementioned preferred class have the formula

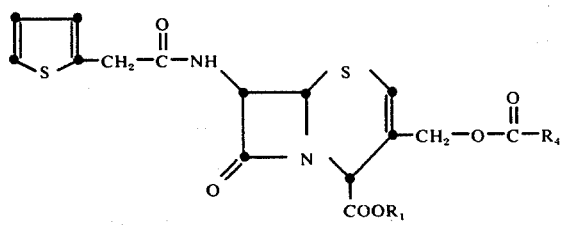

in which $R_1$ is a carboxylic acid protecting group and $R_4$ is $C_1$-$C_4$ alkyl, and, more preferably, methyl.

The conversion of the 3-exomethylenecepham sulfoxide to the corresponding 3-acyloxymethyl-$\Delta^2$-cephem is accomplished by reaction with a mixture of a carboxylic acid of the formula

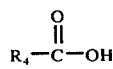

and its corresponding anhydride. The group $R_4$ in the forgoing carboxylic acid is a $C_1$-$C_4$ alkyl. Thus, the carboxylic acids which can be employed include acetic acid, propionic acid, n-butyric acid, isobutyric acid, valeric acid, trimethylacetic acid, α-methylbutyric acid, β-methylbutyric acid, and the like. As indicated above, these carboxylic acids are employed in combination with their corresponding symmetrical acid anhydride. Thus, for example, a mixture of acetic acid and acetic anhydride is employed in the process of this invention when it is intended that the product which is produced be a 3-acetoxymethyl-$\Delta^2$-cephem ester. When it is intended that the product be a 3-propionoxymethyl-$\Delta^2$-cephem ester, a mixture of propionic acid and propionic anhydride is employed. It is highly preferred, in the process of this invention, that a mixture of acetic acid and acetic anhydride be employed, thereby producing, as product, a 3-acetoxymethyl-$\Delta^2$-cephem ester.

In carrying out the process of this invention, the 3-exomethylenecepham sulfoxide is mixed with a mixture of the selected carboxylic acid and its corresponding anhydride. Generally, the volume ratio of carboxylic acid to anhydride is from about 1:20 to about 20:1, and, preferably, from about 1:4 to about 4:1. Typically, the 3-exomethylenecepham sulfoxide is added to the prepared mixture of the carboxylic acid and its corresponding anhydride. The resulting mixture then is heated at a temperature of from about 70° C. to about 130° C. for a time sufficient to achieve coversion to the desired 3-acyloxymethyl-$\Delta^2$-cephem compound. The time necessary to achieve reaction can vary over a wide range, and, typically, will be from about 2 hours to about 80 hours.

In the conversion represented by the process of this invention, the amount of acid-anhydride mixture which is employed generally will be at least about 4 ml. per each millimole of 3-exomethylenecepham sulfoxide. A large excess of the acid-anhydride mixture can be employed without detriment; however, no advantage is apparent from the use of a vast excess of the acid-anhydride mixture. Preferably, therefore, the acid-anhydride mixture is present in an amount of from about 8 ml. to about 25 ml. per each millimole of the 3-exomethylenecepham sulfoxide. It is also possible to employ an inert organic solvent in addition to the acid-anhydride mixture. However, this is not essential, and it does not in any way contribute to the success of the reaction.

Typically and preferably, therefore, the 3-exomethylenecepham sulfoxide ester is added to a 2:1 volume ratio of anhydride to carboxylic acid, and, preferably, of acetic anhydride to acetic acid, in an amount sufficient to produce a mixture of approximately 8 ml. of the anhydride-acid mixture per each millimole of the 3-exomethylenecepham sulfoxide ester. The resulting mixture is heated at a temperature of from about 120° C. to about 130° C. for about two to about four hours after which time substantial completion of the reaction normally will have occurred.

The resulting 3-acyloxymethyl-$\Delta^2$-cephem product is recovered by evaporation of the excess materials and purification of the resulting residue by employing conventional techniques. Such techniques include, for example, chromatographic separation, filtration, crystallization, recrystallization, and other such recognized methods.

Example of conversions which are available in accordance with the process of this invention include:

p-nitrobenzyl 7-maleimido-3-methylenecepham-4-carboxylate-1-oxide to p-nitrobenzyl 7-maleimido-3-acetoxymethyl-2-cephem-4-carboxylate;

2,2,2-trichloroethyl 7-phthalimido-3-methylenecepham-4-carboxylate-1-oxide to 2,2,2-trichloroethyl 7-phthalimido-3-propionoxymethyl-2-cephem-4-carboxylate;

benzyl 7-formamido-3-methylenecepham-4-carboxylate-1-oxide to benzyl 7-formamido-3-butyroxymethyl-2-cephem-4-carboxylate;

2,2,2-trichloroethyl 7-acetamido-3-methylenecepham-4-carboxylate-1-oxide to 2,2,2-trichloroethyl 7-acetamido-3-acetoxymethyl-2-cephem-4-carboxylate;

p-nitrobenzyl 7-butyramido-3-methylenecepham-4-carboxylate-1-oxide to p-nitrobenzyl 7-butyramido-3-acetoxymethyl-2-cephem-4-carboxylate;

p-methoxybenzyl 7-chloroacetamido-3-methylenecepham-4-carboxylate-1-oxide to p-methoxybenzyl 7-chloroacetamido-3-propionoxymethyl-2-cephem-4-carboxylate;

p-nitrobenzyl 7-(4'-nitrobenzyloxycarbamido)-3-methylenecepham-4-carboxylate-1-oxide to p-nitrobenzyl 7-(4'-nitrobenzyloxycarbamido)-3-isobutyroxymethyl-2-cephem-4-carboxylate;

p-chlorophenacyl 7-benzyloxycarbamido-3-methylene-cepham-4-carboxylate-1-oxide to p-chlorophenacyl 7-benzyloxycarbamido-3-valeroxymethyl-2-cephem-4-carboxylate;

succinimidomethyl 7-(benzyloxycarbamido)-3-methylenecepham-4-carboxylate-1-oxide to succinimidomethyl 7-(benzyloxycarbamido)-3-acetoxymethyl-2-cephem-4-carboxylate;

2,2,2-trichloroethyl 7-(2',2',2'-trichloroethoxycarbamido)-3-methylenecepham-4-carboxylate-1-oxide to 2,2,2-trichloroethyl 7-(2',2',2'-trichloroethoxycarbamido)-3-propionoxymethyl-2-cephem-4-carboxylate;

acetoxymethyl 7-(4'-methoxybenzyloxycarbamido)-3-methylenecepham-4-carboxylate-1-oxide to acetoxymethyl 7-(4'-methoxybenzyloxycarbamido)-3-acetoxymethyl-2-cephem-4-carboxylate;

benzyl 7-phenoxyacetamido-3-methylenecepham-4-carboxylate-1-oxide to benzyl 7-phenoxyacetamido-3-acetoxymethyl-2-cephem-4-carboxylate;

phthalimidomethyl 7-benzamido-3-methylenecepham-4-carboxylate-1-oxide to phthalimidomethyl 7-benzamido-3-α-methylbutyroxymethyl-2-cephem-4-carboxylate;

phenacyl 7-(4'-chlorobenzamido)-3-methylenecepham-4-carboxylate-1-oxide to phenacyl 7-(4'-chlorobenzamido)-3-acetoxymethyl-2-cephem-4-carboxylate;

p-chlorophenacyl 7-(3'-bromobenzamido)-3-methylene-cepham-4-carboxylate-1-oxide to p-chlorophenacyl 7-(3'-bromobenzamido)-3-acetoxymethyl-2-cephem-4-carboxylate;

pivaloyloxymethyl 7-(4'-nitrobenzamido)-3-methylenecepham-4-carboxylate-1-oxide to pivaloyloxymethyl 7-(4'-nitrobenzamido)-3-propionoxymethyl-2-cephem-4-carboxylate;

acetoxymethyl 7-(2'-cyanobenzamido)-3-methylenecepham-4-carboxylate-1-oxide to acetoxymethyl 7-(2'-cyanobenzamido)-3-acetoxymethyl-2-cephem-4-carboxylate;

succinimido 7-(4'-trifluoromethylbenzamido)-3-methylenecepham-4-carboxylate-1-oxide to succinimidomethyl 7-(4'-trifluoromethylbenzamido)-3-β-methylbutyroxymethyl-2-cephem-4-carboxylate;

phthalimidomethyl 7-(3'-methylbenzamido)-3-methylenecepham-4-carboxylate-1-oxide to phthalimidomethyl 7-(3'-methylbenzamido)-3-acetoxymethyl-2-cephem-4-carboxylate;

2,2,2-tribromoethyl 7-(2'-methoxybenzamido)-3-methylenecepham-4-carboxylate-1-oxide to 2,2,2-tribromoethyl 7-(2'-methoxybenzamido)-3-valeroxymethyl-2-cephem-4-carboxylate;

propionoxymethyl 7-phenylacetamido-3-methylenecepham-4-carboxylate-1-oxide to propionoxymethyl 7-phenylacetamido-3-acetoxymethyl-2-cephem-4-carboxylate;

p-nitrobenzyl 7-(2'-thienylacetamido)-3-methylenecepham-4-carboxylate-1-oxide to p-nitrobenzyl 7-(2'-thienylacetamido)-3-propionoxymethyl-2-cephem-4-carboxylate;

p-methoxybenzyl 7-phenylacetamido-3-methylenecepham-4-carboxylate-1-oxide to p-methoxybenzyl 7-phenylacetamido-3-butyroxymethyl-2-cephem-4-carboxylate;

2,2,2-trichloroethyl 7-phenoxyacetamido-3-methylenecepham-4-carboxylate-1-oxide to 2,2,2-trichloroethyl 7-phenoxyacetamido-3-acetoxymethyl-2-cephem-4-carboxylate;

p-nitrobenzyl 7-(2',5'-dichlorophenylacetamido)-3-methylenecepham-4-carboxylate-1-oxide to p-nitrobenzyl 7-(2',5'-dichlorophenylacetamido)-3-acetoxymethyl-2-cephem-4-carboxylate;

benzyl 7-(3'-bromophenoxyacetamido)-3-methylenecepham-4-carboxylate-1-oxide to benzyl 7-(3'-bromophenoxyacetamido)-3-isobutyroxymethyl-2-cephem-4-carboxylate;

p-bromophenacyl 7-(4'-chlorophenylacetamido)-3-methylenecepham-4-carboxylate-1-oxide to p-bromophenacyl 7-(4'-chlorophenylacetamido)-3-acetoxymethyl-2-cephem-4-carboxylate;

pivaloyloxymethyl 7-(3'-chlorophenoxyacetamido)-3-methylenecepham-4-carboxylate-1-oxide to pivaloyloxymethyl 7-(3'-chlorophenoxyacetamido)-3-acetoxymethyl-2-cephem-4-carboxylate;

p-nitrobenzyl 7-(4'-nitrophenylacetamido)-3-methylenecepham-4-carboxylate-1-oxide to p-nitrobenzyl 7-(4'-nitrophenylacetamido)-3-propionoxymethyl-2-cephem-4-carboxylate;

p-methoxybenzyl 7-(4'-nitrophenoxyacetamido)-3-methylenecepham-4-carboxylate-1-oxide to p-methoxybenzyl 7-(4'-nitrophenoxyacetamido)-3-acetoxymethyl-2-cephem-4-carboxylate;

p-nitrobenzyl 7-(3'-cyanophenylacetamido)-3-methylenecepham-4-carboxylate-1-oxide to p-nitrobenzyl 7-(3'-cyanophenylacetamido)-3-butyroxymethyl-2-cephem-4-carboxylate;

p-bromophenacyl 7-(2'-cyanophenoxyacetamido)-3-methylenecepham-4-carboxylate-1-oxide to p-bromophenacyl 7-(2'-cyanophenoxyacetamido)-3-acetoxymethyl-2-cephem-4-carboxylate;

propionoxymethyl 7-(4'-trifluoromethylphenylacetamido)-3-methylenecepham-4-carboxylate-1-oxide to propionoxymethyl 7-(4'-trifluoromethylphenylacetamido)-3-acetoxymethyl-2-cephem-4-carboxylate;

2,2,2-tribromomethyl 7-(3'-trifluoromethylphenoxyacetamido)-3-methylenecepham-4-carboxylate-1-oxide to 2,2,2-tribromomethyl 7-(3'-trifluoromethylphenoxyacetamido)-3-propionoxymethyl-2-cephem-4-carboxylate;

2,2,2-trichloroethyl 7-(2'-ethylphenylacetamido)-3-methylenecepham-4-carboxylate-1-oxide to 2,2,2-trichloroethyl 7-(2'-ethylphenylacetamido)-3-acetoxymethyl-2-cephem-4-carboxylate;

acetoxymethyl 7-(4'-isopropylphenoxyacetamido)-3-methylenecepham-4-carboxylate-1-oxide to acetoxymethyl 7-(4'-isopropylphenoxyacetamido)-3-butyroxymethyl-2-cephem-4-carboxylate;

benzyl 7-(3'-ethoxyphenylacetamido)-3-methylenecepham-4-carboxylate-1-oxide to benzyl 7-(3'-ethoxyphenylacetamido)-3-isobutyroxymethyl-2-cepham-4-carboxylate;

p-nitrobenzyl 7-(4'-isopropoxyphenoxyacetamido)-3-methylenecepham-4-carboxylate-1-oxide to p-nitrobenzyl 7-(4'-isopropoxyphenoxyacetamido)-3-valeroxymethyl-2-cephem-4-carboxylate;

p-nitrobenzyl 7-(α-2,2,2-trichloroethoxycarbonylphenylacetamido)-3-methylenecepham-4-carboxylate-1-oxide to p-nitrobenzyl 7-(α-2,2,2-trichloroethoxycarbonylphenylacetamido)-3-α-methylbutyroxymethyl-2-cephem-4-carboxylate;

p-methoxybenzyl 7-(α-phenacyloxycarbonylphenylacetamido)-3-methylenecephem-4-carboxylate-1-oxide to p-methoxybenzyl 7-(α-phenacyloxycarbonylphenylacetamido)-3-acetoxymethyl-2-cephem-4-carboxylate;

benzyl 7-(2-thienyl-α-benzyloxycarbonylacetamido)-3-methylenecepham-4-carboxylate-1-oxide to benzyl 7-(2-thienyl-α-benzyloxycarbonylacetamido)-3-β-methylbutyroxymethyl-2-cephen-4-carboxylate;

2,2,2-trichloroethyl 7-(α-p-nitrobenzyloxycarbonylphenylacetamido)-3-methylenecepham-4-carboxylate-1-oxide to 2,2,2-trichloroethyl 7-(α-p-nitrobenzyloxycarbonylphenylacetamido)-3-acetoxymethyl-2-cephem-4-carboxylate;

p-nitrobenzyl 7-(α-benzyloxycarbonylphenylacetamido)-3-methylene-cephem-4-carboxylate-1-oxide to p-nitrobenzyl 7-(α-benzyloxycarbonylphenylacetamido)-3-acetoxymethyl-2-cephem-4-carboxylate;

p-methoxybenzyl 7-(α-4-methoxybenzyloxycarbonylphenylacetamido)-3-methylenecepham-4-carboxylate-1-oxide to p-methoxybenzyl 7-(α-4-methoxybenzyloxycarbonylphenylacetamido)-3-propionoxymethyl-2-cephem-4-carboxylate;

p-nitrobenzyl 7-(2'-thienyl-α-p-nitrobenzyloxycarbonylacetamido)-3-methylenecephem-4-carboxylate-1-oxide to p-nitrobenzyl 7-(2'-thienyl-α-p-nitrobenzyloxycarbonylacetamido)-3-acetoxymethyl-2-cephem-4-carboxylate;

p-nitrobenzyl 7-(2'-thienylacetamido)-3-methylenecepham-4-carboxylate-1-oxide to p-nitrobenzyl 7-(2'-thienylacetamido)-3-acetoxymethyl-2-cephem-4-carboxylate;

benzyl 7-(3'-thienylacetamido)-3-methylenecepham-4-carboxylate-1-oxide to benzyl 7-(3'-thienylacetamido)-3-acetoxymethyl-2-cephem-4-carboxylate;

p-methoxybenzyl 7-(2'-furylacetamido)-3-methylenecepham-4-carboxylate-1-oxide to p-methoxybenzyl 7-(2'-furylacetamido)-3-propionoxymethyl-2-cephem-4-carboxylate;

p-chlorophenacyl 7-(3'-furylacetamido)-3-methylenecepham-4-carboxylate-1-oxide to p-chlorophenacyl 7-(3'-furylacetamido)-3-butyroxymethyl-2-cephem-4-carboxylate;

succinimidomethyl 7-(2'-thiazolylacetamido)-3-methylenecepham-4-carboxylate-1-oxide to succinimidomethyl 7-(2'-thiazolylacetamido)-3-valeroxymethyl-2-cephem-4-carboxylate;

p-nitrobenzyl 7-(5'tetrazolylacetamido)-3-methylenecepham-4-carboxylate-1-oxide to p-nitrobenzyl 7-(5'-tetrazolylacetamido)-3-α-methylbutyroxymethyl-2-cephem-4-carboxylate;

p-nitrobenzyl 7-(1'-tetrazolylacetamido)-3-methylenecepham-4-carboxylate-1-oxide to p-nitrobenzyl 7-(1'-tetrazolylacetamido)-3-acetoxymethyl-2-cephem-4-carboxylate;

p-methoxybenzyl 7-(4'-isoxazolylacetamido)-3-methylenecepham-4-carboxylate-1-oxide to p-methoxybenzyl 7-(4'-isoxazolylacetamido)-3-acetoxymethyl-2-cephem-4-carboxylate;

benzyl 7-[3'-(2''-chlorophenyl)-5'-methylisoxazol-4'-ylcarbamido]-3-methylenecepham-4carboxylate-1-oxide to benzyl 7-[3'-(2''-chlorophenyl)-5'-methylisoxazol-4'-ylcarbamido]-3-β-methylbutyroxymethyl-2-cephem-4-carboxylate;

p-nitrobenzyl 7-(2',2'-dimethyl-3'-acetyl-5'-oxo-4'-phenylimidazolidin-1'-yl)-3-methylenecepham-4-carboxylate-1-oxide to p-nitrobenzyl 7-(2',2'-dimethyl-3'-acetyl-5'-oxo-4'-phenylimidazolidin-1'-yl)-3-acetoxymethyl-2-cephem-4-carboxylate;

benzyl 7-[2',2'-dimethyl-3'-nitroso-5'-oxo-4'-(4''-chlorophenyl)imidazolidin-1'-yl]-3-methylenecepham-4-carboxylate-1-oxide to benzyl 7-[2',2'-dimethyl-3'-nitroso-5'-oxo-4'-(4''-chlorophenyl)imidazolidin-1'-yl]-3-acetoxymethyl-2-cephem-4-carboxylate; and the like.

The 3-acyloxymethyl-$\Delta^2$-cephem esters produced by the process of this invention are useful as intermediates in the preparation of antibiotically active cephalosporins. The $\Delta^2$-cephem product is treated in accordance with the method described in U.S. Pat. No. 3,705,897 to produce the corresponding $\Delta^3$-cephem ester. The described method, although specifically directed to 3-halomethyl-$\Delta^2$-cephem compounds, nevertheless, is fully applicable to the 3-acyloxymethyl-$\Delta^2$-cephem esters produced by the process of this invention. The method which is described in the U.S. patent involves oxidation of the $\Delta^2$-cephem compound using an oxidizing agent to produce a cephem sulfoxide. With respect to at least a portion of the oxidized product, isomerization of the double bond from the $\Delta^2$ position to the $\Delta^3$ position occurs. Where necessary, isomerization of the double bond of the sulfoxide can be completed by treating the product with a tertiary amine. The resulting $\Delta^3$-cephem sulfoxide is reduced to the corresponding sulfide by treatment with any of a number of defined reducing agents. When this method is applied to the products from the process of this invention, a 3-acyloxymethyl-$\Delta^3$-cephem ester is obtained.

At this point, it is noteworthy to recognize that, in addition to the $\Delta^2$-cephem product obtained from the process of this invention, a minor amount of the corresponding $\Delta^3$-cephem compound generally will be produced. The two products, of course, can be separated using one or more of any of several readily recognized techniques, such as those described above. However, since the customary purpose for generating the $\Delta^2$-cephem compound will contemplate its ultimate conversion to a $\Delta^3$-cephem antibiotically active compound, no separation is necessary. The mixture of the $\Delta^2$-cephem and the $\Delta^3$-cephem, as obtained from the process of the invention, can be treated, under the conditions described above, to produce the desired $\Delta^3$-cephem compound. The $\Delta^3$-cephem present in the starting material as contaminant, will simply be oxidized to the sulfoxide and reduced back to the sulfide, and thus be recovered as the desired product.

The corresponding $\Delta^3$-cephem acids exhibit potent antibacterial activity. Such compounds are available by cleavage of the ester function. De-esterification can be achieved, depending upon the nature of the protecting group, by any of several recognized procedures, including (1) treatment with an acid such as trifluoroacetic acid, formic acid, hydrochloric acid, or the like; (2) treatment with zinc and an acid such as formic acid, acetic acid, or hydrochloric acid; or (3) hydrogenation in the presence of palladium, platinum, rhodium, or a compound thereof, in suspension, or on a carrier such as barium sulfate, carbon, alumina, or the like. Furthermore, the resulting 3-acyloxymethyl-$\Delta^3$-cephem acid is convertible to other antibiotically active cephalosporins by cleavage of the amido or imido group in the 7-position to the free 7-amino group with subsequent reacylation to produce any of a number of recognized active cephalosporin antibiotics. Cleavage and reacylation methods are well recognized in the cephalosporin art.

By the process of this invention, therefore, several widely recognized cephalosporin antibiotics are available. These include, for example, the sodium salt of 7-(2-thienylacetamido)-3-acetoxymethyl-3-cephem-4-carboxylic acid (cephalothin); 7-(α-aminophenylacetamido)-3-acetoxymethyl-3-cephem-4-carboxylic acid (cephaloglycin); the sodium salt of 7-cyanoacetamido-3-acetoxymethyl-3-cephem4-carboxylic acid (cephacetrile); and the like.

This invention is further illustrated by reference to the examples which follow. It is not intended that this invention be limited in scope by reason of any of the examples provided herein.

EXAMPLE 1

To a mixture of 33 ml. of acetic acid and 66 ml. of acetic anhydride were added 6 gms. (12 mmoles) of p-nitrobenzyl 7-phenoxyacetamido-3-methylenecepham-4-carboxylate1-oxide. The mixture was maintained under a slow stream of nitrogen and then was brought to reflux (about 126° C). Progress of the reaction was followed by thin-layer chromatography (TLC) using a 1:1 mixture of benzene and ethyl acetate on silica gel plates. The reaction was complete in about 2.5 hours, after which time the resulting reddish solution was evaporated to a dark tar. The resulting residue was dissolved in 50 ml. of ethyl acetate. The ethyl acetate solution was washed three times with 50 ml. each of saturated sodium bicarbonate solution and once with 50 ml. of saturated sodium chloride solution. The ethyl acetate layer then was dried over magnesium sulfate, treated with activated carbon, and filtered through silica gel. The filtrate was evaporated to obtain 5.8 gms. (89 percent) of a 3:1 mixture of p-nitrobenzyl 7-phenoxyacetamido-3-acetoxymethyl-2-cephem-4-carboxylate and p-nitrobenzyl 7-phenoxyacetamido-3-acetoxymethyl-3-cephem-4-carboxylate as a light yellow foam.

nmr (3:1 mixture of $\Delta^2$ and $\Delta^3$) $\delta$ (CDCl$_3$) 6.5 (broad s, 0.75, $\Delta^2$-C$_2$); 5.8 (dd, 1, C$_7$-H); 4.6 (s, 2, C$_7$ methylene); 3.6 (broad s, 0.5, $\Delta^3$-C$_2$); and 2.1-2.2 (ss, 3, $\Delta^2$ and $\Delta^3$ C$_3$, acetoxy).

EXAMPLE 2-6

The reaction of Example 1 was reported under varying conditions as follows:

| Ex. No. | Sulfoxide, gms. | Acetic anhydride, ml. | Acetic Acid, ml. | Temp., ° C. | Time, hrs. | Product, gms. |
|---|---|---|---|---|---|---|
| 2 | 3 | 34 | 16 | 105 | 15 | 2.6 |
| 3 | 3 | 25 | 100 | 118 | 16 | 2.5 |
| 4 | 6 | 50 | 50 | 95 | 68 | 5.4 |
| 5 | 3 | 25 | 25 | 124 | 6 | 2.5 |
| 6 | 3 | 40 | 10 | 131 | 1.5 | 2.15 |

EXAMPLE 7

To 170 ml. of methylene chloride were added 5.65 gms. of the product from Example 1 and 20 ml. of isopropyl alcohol. The mixture was cooled to about 0° C. A solution of 2.12 gms. of 85 percent technical grade m-chloroperbenzoic acid in 55 ml. of methylene chloride was added dropwise rapidly. The progress of the reaction was followed by TLC. After 45 minutes, the methylene chloride mixture was washed three times with 100 ml. of aqueous sodium bicarbonate solution. The methylene chloride layer then was dried over magnesium sulfate and treated with activated carbon. The methylene chloride solution then was cooled in an ice bath, and petroleum ether was added slowly to obtain, by crystallization, 4.39 gms. (76 percent) of p-nitrobenzyl 7-phenoxyacetamido-3-acetoxymethyl-3-cephem-4-carboxylate-1-oxide.

EXAMPLE 8

To 75 ml. of N,N-dimethylformamide (DMF) were added 2.70 gms. of the product from Example 7. The mixture was cooled to −80° C., and 1.6 ml. of phosphorous trichloride was added in one portion. The resulting mixture was stirred for 10 minutes at −80° C., and then was warmed to about 0° C. using an ice water bath. Stirring of the mixture was continued for about 25 minutes, and the resulting orange solution then was poured onto ice. A precipitate formed and was removed by filtration, washed thoroughly with water, and dried to give 2.35 gms. (89.5 percent) of p-nitrobenzyl 7-phenoxyacetamido-3-acetoxymethyl-3-cephem-4-carboxylate.

EXAMPLE 9

To a mixture of 5 ml. of acetic anhydride and 20 ml. of acetic acid were added 600 mg. of 2,2,2-trichoroethyl 7-(p-nitrobenzyloxycarbonylamino)-3-methylenecepham-4-carboxylate-1-oxide. The resulting mixture was stirred at 110° C. for 6 hours. The reaction mixture then was cooled, and the solvent was evaporated. The resulting residue was dissolved in ethyl acetate, and the ethyl acetate solution was washed with saturated aqueous sodium bicarbonate. The organic layer then was dried over magnesium sulfate, evaporated, and the residue was chromatographed over silica gel to obtain 100 mg. of a 6:1 mixture of 2,2,2-trichloroethyl 7-(p-nitrobenzyloxycarbonylamino)-3-acetoxymethyl-2-cephem-4-carboxylate and 2,2,2-trichloroethyl 7-(p-nitrobenzyloxycarbonylamino)-3-acetoxymethyl-3-cephem-4-carboxylate.

nmr (6:1 mixture of $\Delta^2$ and $\Delta^3$) $\delta$ (CDCl$_3$) 6.45 (broad s, 0.83, $\Delta^2$-C$_2$); 4.75 (s, 2, trichloroethyl); 4.65 (broad s, 1.66, $\Delta^2$ C$_3$'-methylene); 3.5 (broad s, 0.34, $\Delta^3$-C$_2$); and 2.10–2.15 (broad s, 3, $\Delta^2$ and $\Delta^3$ C$_3$'-acetoxy).

EXAMPLE 10

To a mixture of 5 ml. of acetic anhydride and 20 ml. of acetic acid were added 600 mg. of p-nitrobenzyl 7-(2-thienylacetamido)-3-methylenecepham-4-carboxylate 1-oxide. The resulting mixture was stirred at 110° C. for four hours. The mixture was cooled, evaporated, and the resulting residue was dissolved in ethyl acetate. The ethyl acetate solution was washed with aqueous sodium bicarbonate and dried over magnesium sulfate. The solvent was evaporated, and the residue was chromatographed over silica gel to obtain 110 mg. of p-nitrobenzyl 7-(2-thienylacetamido)-3-acetoxymethyl-2-cephem-4-carboxylate.

nmr $\delta$ (CDCl$_3$) 6.4 (broad s, 1, $\Delta^2$-C$_2$); 5.6 (dd, 1, C$_7$-H); 4.6 (broad s, 2, C$_3$'-methylene); 3.8 (s, 2, C$_7$-methylene); and 2.05 (s, 3, C$_3$'-acetoxy).

EXAMPLE 11

To a mixture of 5 ml. of propionic anhydride and 20 ml. of propionic acid were added 600 mg. of p-nitrobenzyl 7-phenoxyacetamido-3-methylenecepham-4-carboxylate-1-oxide. The mixture was stirred at 130° C. for 6 hours. The resulting mixture was cooled, and the solvent was removed in vacuo. The resulting residue was dissolved in 150 ml. of ethyl acetate, and the ethyl acetate solution was washed with saturated aqueous sodium bicarbonate. The ethyl acetate layer was separated and dried over magnesium sulfate. The solvent was evaporated, and the residue was chromatographed on silica gel to obtain 166 mg. of p-nitrobenzyl 7-phenoxyacetamido-3-propionyloxymethyl-2-cephem-4-carboxylate.

nmr $\delta$ (CDCl$_3$) 6.45 (broad s, 1, $\Delta^2$-C$_2$); 5.7 (dd, 1, C$_7$-H); 2.3 (q, 2, methylene or propionoxy); and 1.1 (t, 3, methyl of propionoxy).

I claim:
1. A process for preparing a compound of the formula

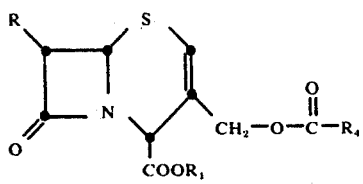

which comprises reacting a 3-exomethylenecepham sulfoxide of the formula

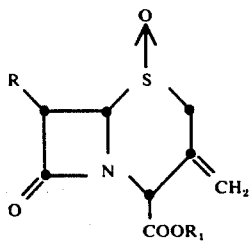

with a mixture of a carboxylic acid of the formula

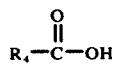

and the corresponding anhydride of said carboxylic acid at a temperature of from about 70° C. to about 130° C., in which, in the above formulae, $R_4$ is $C_1$–$C_4$ alkyl, $R_1$ is a carboxylic acid protecting group, and R is 1. an imido group of the formula

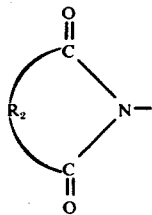

in which $R_2$ is $C_2$–$C_4$ alkenylene or 1,2-phenylene;

2. an amido group of the formula

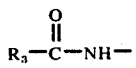

in which $R_3$ is
  a. hydrogen, $C_1$–$C_3$ alkyl, halomethyl, benzyloxy, 4-nitrobenzyloxy, 2,2,2-trichloroethoxy, 4-methoxybenzyloxy, 3-(2-chlorophenyl)-5-methyl-isoxazol-4-yl;
  b. the group R' in which R' is phenyl or phenyl substituted with 1 or 2 halogens, nitro, cyano, trifluoromethyl, $C_1$–$C_4$ alkyl, or $C_1$–$C_4$ alkoxy;
  c. a group of the formula R'—(O)$_m$—CH$_2$— in which R' is as defined above and m is 0 or 1;
  d. a group of the formula

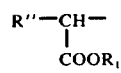

in which
R" is R' as defined above, 2-thienyl, or 3-thienyl, and $R_1$ is as defined above; or
  e. a group of the formula R'"-CH$_2$-in which R'" is 2-thienyl, 3-thienyl, 2-furyl, 3-furyl, 2-thiazolyl, 5-tetrazolyl, 1-tetrazolyl, or 4-isoxazolyl; or R is 3. an imidazolidinyl group of the formula

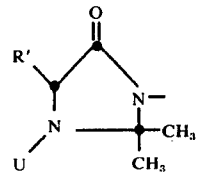

in which R' is as defined above and U is nitroso or acetyl.

2. Process of claim 1, in which R is a group of the formula

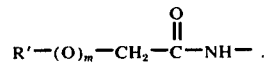

3. Process of claim 2, in which R' is phenyl.
4. Process of claim 3, in which m is 0.
5. Process of claim 3, in which m is 1.
6. Process of claim 1, in which R is a group of the formula

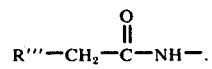

7. Process of claim 6, in which R'" is 2-thienyl.
8. Process of claim 1, in which $R_1$ is 2,2,2-trihaloethyl, benzyl, p-nitrobenzyl, succinimidomethyl, phthalimidomethyl, p-methoxybenzyl, $C_2$–$C_6$ alkanoyloxymethyl, dimethylallyl, phenacyl, or p-halophenacyl.
9. Process of claim 8, in which $R_1$ is benzyl, p-nitrobenzyl, p-methoxybenzyl, 2,2,2-trichloroethyl, phenacyl, p-chlorphenacyl, or p-bromophenacyl.
10. Process of claim 1, in which

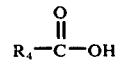

is acetic acid.
11. Process of claim 10, in which the volume ratio of the carboxylic acid to the anhydride is from about 1:20 to about 20:1.
12. Process of claim 11, in which the amount of the mixture of carboxylic acid and anhydride which is employed is at least about 4 ml. per millimole of 3-exomethylenecepham sulfoxide.
13. Process of claim 12, in which the 3-exoethylenecepham sulfoxide is added to a 2:1 volume ratio of acetic anhydride to acetic acid in an amount sufficient to produce a mixture of approximately 8 ml. of the anhydride-acid mixture per each millimole of the 3-exomethylenecepham sulfoxide, and the resulting mixture is heated at a temperature of from about 120° C. to about 130° C. for from about 2 to about 4 hours.

* * * * *